United States Patent
Yadav et al.

(10) Patent No.: US 10,414,952 B2
(45) Date of Patent: Sep. 17, 2019

(54) BIO-FIBER GUM HYDROLYSATES AND PROCESSES OF PRODUCING

(71) Applicants: The Unites States of America, as represented by the Secretary of Agriculture, Washington, DC (US); AgriFiber Solutions, LLC, Mundelein, IL (US)

(72) Inventors: Madhav P Yadav, North Wales, PA (US); Arland T. Hotchkiss, Ambler, PA (US); Kyle Hanah, Mount Prospect, IL (US); Madhuvanti S. Kale, Fremont, CA (US); David Johnston, Wyndmoor, PA (US)

(73) Assignees: The United States of America, as represented by the Secretary of Agriculture, Washington, DC (US); AgriFiber Solutions, LLC, Mundelein, IL (US)

( * ) Notice: Subject to any disclaimer, the term of this patent is extended or adjusted under 35 U.S.C. 154(b) by 199 days.

(21) Appl. No.: 15/589,527

(22) Filed: May 8, 2017

(65) Prior Publication Data

US 2017/0321091 A1 Nov. 9, 2017

Related U.S. Application Data

(60) Provisional application No. 62/333,456, filed on May 9, 2016.

(51) Int. Cl.
*C09J 105/14* (2006.01)
*C08B 37/00* (2006.01)
*C12P 19/14* (2006.01)
*C12P 19/04* (2006.01)

(52) U.S. Cl.
CPC ......... *C09J 105/14* (2013.01); *C08B 37/0057* (2013.01); *C12P 19/04* (2013.01); *C12P 19/14* (2013.01); *C12Y 302/01008* (2013.01)

(58) Field of Classification Search
None
See application file for complete search history.

(56) References Cited

U.S. PATENT DOCUMENTS

| 2,019,056 | A | * | 10/1935 | Osgood | C09J 105/14 156/336 |
| 2014/0017376 | A1 | * | 1/2014 | Yadav | C08B 37/0003 426/542 |
| 2018/0134741 | A1 | * | 5/2018 | Falck | A61K 31/702 |

* cited by examiner

*Primary Examiner* — Mary Lynn F Theisen
(74) *Attorney, Agent, or Firm* — Ediz Yonter; John D. Fado (57) ABSTRACT

Compositions comprising bio-fiber gum hydrolysate and processes to hydrolyze bio-fiber gum (BFG), involving dissolving BFG in a solvent to form a solution, heating the solution and adding endoxylanase to the solution or adding endoxylanase to the solution and heating the solution, incubating the solution to form a solution containing BFG hydrolysate, boiling the solution containing BFG hydrolysate to inactivate the endoxylanase, and separating the BFG hydrolysate from the liquid in the solution containing BFG hydrolysate.

27 Claims, 4 Drawing Sheets
(1 of 4 Drawing Sheet(s) Filed in Color)

BIO-FIBER GUM HYDROLYSATES AND PROCESSES OF PRODUCING

CROSS REFERENCE TO RELATED APPLICATION

This application claims priority to and the benefit of U.S. Provisional Application Ser. No. 62/333,456, the content of which is incorporated herein by reference in its entirety.

FIELD OF THE INVENTION

This invention relates generally to compositions comprising hydrolyzed bio-fiber gum and processes of producing such compositions. More particularly, the disclosed invention relates to compositions comprising hydrolyzed bio-fiber gum and such compositions produced by processes comprising utilization of enzymatic treatments, in combination with pH and temperature modifications.

BACKGROUND OF THE INVENTION

Arabinoxylans are cell wall polysaccharides abundant in plants of the family Poaceae. The structural commonality of this class of polysaccharides is the β-(1,4) linked D-xylopyranose backbone with α-L-arabinofuranose side chains linked to O-2 and/or O-3 positions of the xylose residues. A large degree of structural heterogeneity is imparted by the presence of other sugars, including galactose, glucuronic acid, and xylose in the branches. Other non-carbohydrate compounds, such as proteins, lipids, and phenolic acids are often strongly associated or covalently linked to the polysaccharide molecules (Yadav, M. P., et al., Journal of Agricultural and Food Chemistry, 55 (3): 943-947 (2007)). The complex structure of arabinoxylans varies greatly by source, with rice and sorghum arabinoxylans having simple structures (widely distributed, single sugar arabinose branches) (Rose, D. J., et al., Journal of Agricultural and Food Chemistry, 58 (1): 493-499 (2009); Verbruggen, M. A., et al., Carbohydrate Research, 306 (1-2): 275-282 (1998)) and corn bran arabinoxylans having highly branched and very complex structures (Huisman, M. M. H., et al., Schols, Carbohydrate Polymers, 43: 269-279 (2000); Rumpagaporn, P., et al., Carbohydrate Polymers, 130: 191-197 (2015); Saulnier, L., et al., Carbohydrate Polymers, 26: 279-287 (1995)).

We have found that using an endoxylanase preparation to hydrolyze Bio-Fiber Gum (BFG), which is a commercially available corn bran arabinoxylan product, surprisingly improved the solubility of the material and also improved the clarity of the solutions. Surprisingly, the hydrolyzates of BFG had emulsifying ability that was as good as that of the original material, which is already known to have excellent emulsifying ability (Yadav, M. P., et al., Bio-based Fiber Gums (BFGs) and processes for producing BFGs, U.S. Patent Application Publication No. 20140017376 A1 (D.N. 0097.12); Yadav, M. P., et al., Journal of Agricultural and Food Chemistry, 56 (11): 4181-4187 (2008)). This finding is of a great significance because such functionality is very desirable in the product development context. Coupled with the surprisingly very low viscosity shown by the hydrolyzates, their emulsifying ability can potentially allow large amounts of beneficial dietary fiber to be included in food systems where emulsification is required, such as beverages, without the need for including additional emulsifying additives. The enzyme concentration used in the hydrolysis process was seen to have a surprisingly significant effect on the molecular properties and rheological behavior of the hydrolyzates.

SUMMARY OF THE INVENTION

Disclosed are processes to hydrolyze bio-fiber gum (BFG), involving dissolving BFG in a solvent at a pH of about 2.5 to about 7 to form a solution, heating the solution to a temperature from about 20° C. to about 70° C. and adding endoxylanase to the solution or adding endoxylanase to the solution and heating the solution to a temperature from about 20° C. to about 70° C., incubating the solution to a temperature from about 20° C. to about 70° C. for about 30 minutes to about 24 hours to form a solution containing BFG hydrolysate, boiling the solution containing BFG hydrolysate for about 5 minutes to about 30 minutes to inactivate the endoxylanase, and separating the BFG hydrolysate from the liquid in the solution containing BFG hydrolysate. Also disclosed are bio-fiber gum hydrolysates produced by the processes disclosed herein.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Disclosed are processes to hydrolyze bio-fiber gum (BFG), (1) involving dissolving BFG in a solvent at a pH of about 2.5 to about 7 (e.g., 2.5 to 7; preferably about 4 to about 6 (e.g., pH of 4 to 6), more preferably about 5 (e.g., pH of 5)) to form a solution, (2) heating the solution to a temperature from about 20° C. to about 70° C. (e.g., 20° C. to 70° C.; preferably about 30° C. to about 60° C. (e.g., 30° C. to 60° C.), more preferably about 55° C. (e.g., 55° C.)) and adding endoxylanase to the solution or adding endoxylanase to the solution and heating the solution to a temperature from about 20° C. to about 70° C. (e.g., 20° C. to 70° C.); preferably about 30° C. to about 60° C. (e.g., 30° C. to 60° C.), more preferably about 55° C. (e.g., 55° C.)), (3) incubating the solution at a temperature from about 20° C. to about 70° C. (e.g., 20° C. to 70° C.); preferably about 30° C. to about 60° C. (e.g., 30° C. to 60° C.), more preferably about 55° C. (e.g., 55° C.)) for about 30 minutes to about 48 hours (e.g., 30 minutes to 48 hours; preferably about 1 to about 24 hours (1 to 24 hours), more preferably about 1 to about 12 hours (1 to 12 hours) to form a solution containing BFG hydrolysate, (4) boiling the solution containing BFG hydrolysate for about 5 minutes to about 30 minutes (e.g., 5 to 30 minutes; preferably about 10 minutes (10 minutes)) to inactivate the endoxylanase, and (5) separating (e.g., centrifugation at about 5,000 g (e.g., 5,000 g) at about 4° C. (e.g., 4° C.) for about 15 minutes (15 minutes) to obtain a clear supernatant) the BFG hydrolysate from the liquid in the solution containing BFG hydrolysate. The solvent may be, for example, water or a buffer such as sodium acetate buffer although a buffer is not necessary in order to carry out the reaction so long as the pH is maintained at a suitable value for the enzyme to function.

Also disclosed are bio-fiber gum hydrolysates produced by the processes described herein. The bio-fiber gum hydrolysates (e.g., from corn) have the following properties: molecular weight of about 200 Da to about 40 kDa (e.g., 200 Da to 40 kDa), $M_w/M_n$ of about 1.3 to about 2 (e.g., 1.3 to 2; preferably about 2 (2)); $Iv_w$ (mL/g) of about 1 to about 0.3 (e.g., 1 to 0.3), $R_{gz}$ (nm) of about 25 to about 20 (e.g., 25 to 20), α of about 0.7 to about 0.9 (e.g., 0.7 to 0.9), and similar emulsifying ability as BFG which has not been hydrolyzed.

Bio-fiber gum as used herein is defined as soluble dietary fiber (SDF), composed of mainly arabinoxylans isolated from plant materials by alkaline treatment. For example, bio-fiber gum (BFG) from corn bran can be produced by the methods described in U.S. Patent Application Publication No. 20140017376. Generally, BFG may be produced by a process involving alkaline treatment of corn or other cereal bran followed by removal of acid insoluble materials from the alkaline extract by adjusting the pH to about 4 using an acid. The low molecular weight materials are removed from the resulting acid soluble materials by ultrafiltration (molecular weight cut off 50 kDa to 100 kDa) and drying the high molecular weight BFG fraction (retentate from ultrafiltration) generally by a spray or drum drying process.

The amounts, percentages and ranges disclosed herein are not meant to be limiting, and increments between the recited amounts, percentages and ranges are specifically envisioned as part of the invention.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

Examples

Bio-Fiber Gum (BFG) from corn bran was a kind gift from Z-Trim Holdings, Inc., and can be produced by the methods described in U.S. Patent Application Publication No. 20140017376. Multifect® GC-Extra, a commercial endoxylanase preparation, was obtained from DuPont Industrial Biosciences (Palo Alto, Calif.). Glacial acetic acid, sodium acetate and sodium nitrate were obtained from Sigma Aldrich (St. Louis, Mo.). All chemicals were reagent grade.

Preparation of BFG hydrolyzates: BFG was dissolved in a 25 mM acetate buffer, pH 5.0, to obtain a 5% solution. The solution was heated to 55° C. with stirring, and the appropriate amount of enzyme preparation was added to get 1, 5 or 10 μL of enzyme preparation per gram of BFG, corresponding to 6, 30, and 60 IU of endoxylanase activity per gram of BFG, respectively. The samples were incubated at 55° C. with shaking for 24 hours. Samples of BFG solution in buffer with no added enzyme, to serve as controls, were also incubated. After the incubation period, the samples were placed in a boiling water bath for 5-7 minutes to inactivate the enzyme, followed by centrifugation at 5000 g at 4° C. for 15 minutes. Finally, the clear supernatant was lyophilized to obtain the hydrolyzed product. The BFG hydrolyzates are henceforth referred to by the enzyme concentration used in their preparation: BFGH-1, BFGH-5, and BFGH-10, while the unhydrolyzed material is referred to as BFG-original.

Measurement of turbidity of BFG hydrolysate solutions: Original BFG and the BFG hydrolyzates were dissolved in water to make 2% solutions. The optical density was measured at 500 nm using a Nanodrop UV-Visible spectrophotometer (Thermo Fisher Scientific, Sunnyvale, Calif.).

Characterization of molecular properties by HPSEC-MALLS-RI-V: The molecular properties were determined following the procedure reported by Yadav et al. (Yadav, M. P., et al., Food Hydrocolloids, 53: 125-133 (2016)) with some modification. In brief, solutions (5 mg/mL) of the BFG or BFGH were prepared in mobile phase (0.05 M $NaNO_3$ and 0.01% $NaN_3$ filtered through a 0.45 μm Millex HV filter (Millipore Corp., Bedford, Mass.). The flow rate for the solvent delivery system, model 1200 series degasser, auto sampler and pump, and UV-1260 Infinity (Agilent Technologies) detector was 0.7 mL/min. The injection volume was 200 μL. Samples were run in triplicate. The column set consisted of two guard columns (6.0 mm×4.0 cm, 12 μm particle size) with one placed before and one after the column set consisting of three model TSK GMPWxl size exclusion columns (7.8 mm×300 mm, 13 μm particle size) (Tosoh Bioscience, Tokyo, Japan) in series. The columns were in a heated water bath set at 35° C. The chromatograph included a HELEOS II multi-angle laser light scattering photometer (MALLS) (Wyatt Technology, Santa Barbara, Calif.) with measurement of quasi elastic scattering (QELS) capability at 120°, model 255-V2 differential pressure viscometer (dPV) and a differential refractive index (dRI)

detector (Wyatt Technology, Santa Barbara, Calif.). The electronic outputs from all the scattering angles measured by the MALLS, dPV and dRI were sent to a directory for processing with ASTRA V 6.1.1.17 software (Wyatt Technology, Santa Barbara, Calif.).

Rheological measurements: Solutions (2%) of the BFG or BFGH samples were prepared in water. The shear viscosity of these samples was measured using an Anton Paar MCR-102 rotational rheometer with concentric cylinder geometry. Measurements were made at 25° C. and the shear rate was varied from 1 $s^{-1}$ to 100 $s^{-1}$.

Emulsifying ability and emulsion stability: The sample for studying emulsion ability and emulsion stability (30 g) was prepared with 1:4 ratio of emulsifier to MCT (octanoic/decanoic acid triglycerides) containing 0.1% sodium benzoate and 0.3% citric acid. A stock solution of emulsifier (27.78 mg/g solution) containing 0.1% (w/w) sodium benzoate (a preservative) and 0.3% (w/w) citric acid was prepared for the emulsification study by slowly adding the calculated amount of BFG or BFGH sample a little at a time with vigorous stirring to a solution of sodium benzoate and citric acid in water at room temperature, and then gently stirring overnight to produce a hydrated, well dissolved and homogeneous solution. The samples for oil-in-water emulsions were prepared in triplicate for each sample by taking 27 g of the above emulsifier stock solution and 3 g of MCT in a glass vial. No weighting agent was added during emulsion preparation to avoid the effects of such agents on the emulsification process. The solution was vortexed and then homogenized using a Polytron™ bench top homogenizer equipped with a 12 mm diameter head (PT 10/35, Brinkmann, Switzerland) at 20,000 rpm for 3 min. The above homogenized emulsion was passed through the EmulsiFlex-B3 high-pressure homogenizer (Avestin Inc., Canada) at 20,000 psi homogenization pressure 3 times to prepare the final emulsions. The particle size distribution of the emulsions was measured using a laser diffraction particle size analyzer (Horiba LA-950). The volume mean diameter was used for describing particle size of emulsions. The emulsification effectiveness was evaluated on the initial particle size of the emulsion at 0 time. The emulsion stability was determined after storing emulsions at 60° C. (acceleration aging test) (Yadav, M. P., et al., Carbohydrate Polymers, 132: 529-536 (2015); Al-Assaf, et al., Food Hydrocolloids, 21 (3): 319-325 (2007)) for 3 and 7 days.

Figure 1:
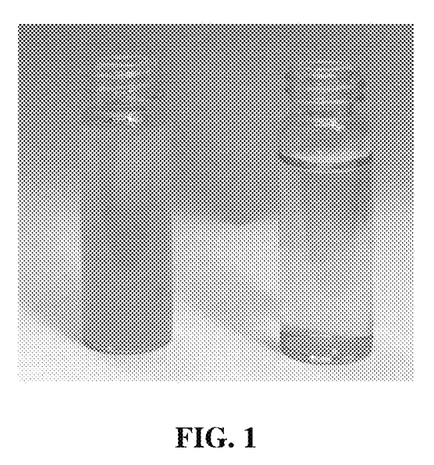
FIG. 1 shows 2% solutions of original BFG (left) and BFG hydrolyzate BFGH-10 (prepared using 10 μL of enzyme preparation per gram of BFG as described below) (right).

Results and Discussion. Yield and solubility of BFG hydrolyzates: Table 1 shows the yield of BFG hydrolyzates from 1 g original BFG by using different enzyme concentrations. From the high yields of the hydrolyzates (80.3 to 88.3%), it was clear that there was not much loss of sample during the hydrolysis process. It was also evident from Table 1 that enzyme concentration did not significantly affect the yield of the product. The hydrolyzates were more readily soluble (roughly less than in about 2-5 minutes) in water than the original BFG, although it must be noted that the original material was also completely soluble in water over about 30-60 minutes, depending on the concentration and volume of solution) of hydration and stirring. The original BFG had a tendency to form fish-eyes, which was not observed at all in the hydrolyzates. The term fish-eyes is well known in the hydrocolloids field, and refers to the tendency of gums to form clumps when added to water that take a long time to break up. Among the hydrolyzates, BFGH-10 formed a very clear solution (FIG. 1), surprisingly unlike the original BFG and the other hydrolyzates, suggesting that the higher concentration of enzyme led to a significant decrease in molecular size resulting in the formation of a clear solution. This was also clear from the measurement of turbidity using optical density at 500 nm (Table 2), which shows that the original BFG formed the most turbid solutions, and the turbidity decreased as the enzyme concentration used for hydrolysis increased. The surprisingly very low values (0.035) of absorbance showed by BFGH-10 are a quantitative indication of its clarity.

TABLE 1

Yield of enzyme hydrolysis products of corn BFG

| Sample | Yield (%) |
|---|---|
| Control sample (no enzyme added) | 88.1 ± 0.02 |
| BFGH-1 | 80.3 ± 2.19 |
| BFGH-5 | 88.9 ± 3.53 |
| BFGH-10 | 88.3 ± 3.51 |

TABLE 2

Turbidity of 2% solutions of original and hydrolyzed BFG products

| Sample | $OD_{500\,nm}$ (Turbidity) |
|---|---|
| BFG-original (Control sample, no enzyme added) | 0.312 ± 0.001 |
| BFGH-1 | 0.135 ± 0.007 |
| BFGH-5 | 0.079 ± 0.002 |
| BFGH-10 | 0.012 ± 0.001 |

Figure 2:
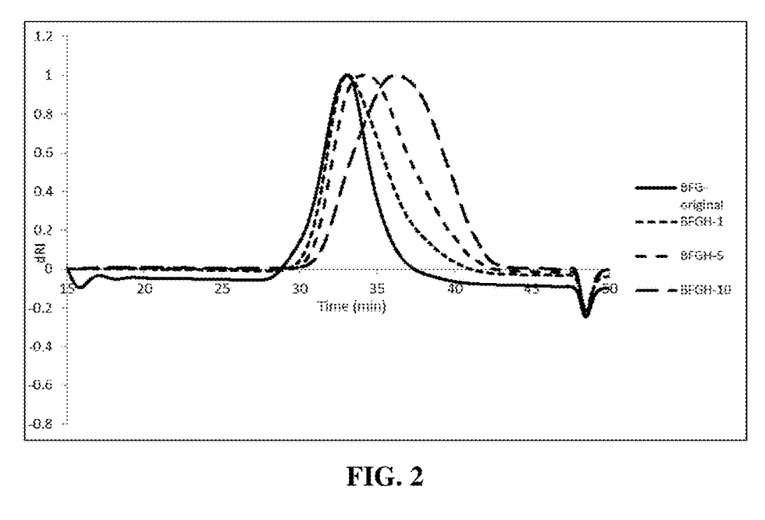
FIG. 2 shows differential refractive index HPSEC chromatograms of BFG and BFG hydrolyzates as described below.

Molecular properties of BFG hydrolyzates: Table 3 summarizes the molecular properties of the original BFG as well as the hydrolyzates, as obtained by HPSEC-MALLS-RI-V. Weight-average molar mass ($M_w$), $M_w/M_n$, $Iv_w$ (mL/g), $Rg_z$ (nm), are the molecular weight, polydispersity index, intrinsic viscosity, and radius of gyration, respectively. They give information about the molecular properties of polymers. $M_w/M_n$ gives information about the uniformity of molecular weight distribution in the polysaccharide molecules, $Iv_w$ is a measure of solute's contribution to its solution viscosity, and $Rg_z$ gives information about molecular size. As the concentration of enzyme was increased the molecular weight and size of the hydrolyzates decreased, with BFGH-10 showing the lowest molecular weight of about 52 kDa. The trends of intrinsic viscosity and radius of gyration of the molecules (Table 3—BFG=Biofiber Gum, $M_w$=weight average molar mass, $M_w/M_n$=polydispersity, $Iv_w$=weight average intrinsic viscosity, $Rg_z$=z average radius of gyration, a=Mark Houwink Constant) were similar to the molecular weight, with higher enzyme concentrations leading to lower intrinsic viscosity and size. The decrease in molecular weight is also clearly illustrated in FIG. 2, which shows the differential refractive index chromatograms of the samples. As the enzyme concentration increased, the dRI peak shifted clearly to the right, indicating decreasing molecular weight. The value of the Mark-Houwink parameter a was surprisingly higher in case of the hydrolyzates than the original BFG, suggesting, without being bound by theory, that the polymer underwent a shape change, becoming more linear as the hydrolysis progressed. The value of a for the original BFG is 0.605, which is well within the range of 0.5-0.8 exhibited by random coil polymers (Picout, D. R., and S. B. Ross-Murphy, Carbohydrate Research, 337: 1781-1784 (2002)). At low enzyme concentrations, the value of a increased, indicating a slightly more linear chain. The reason for this more linear shape is not clear, but, without being bound by theory, it may possibly be due to the unraveling and limited hydrolysis of the unsubstituted xylan regions of the polymer backbone or due to the loss of arabinosyl branches at the acidic pH of the reaction. BFGH-10 showed an a value corresponding to the upper limit of random coil conformation, which is typical of branched arabinoxylan polymers (Dervilly-Pinel, G., et al., Carbohydrate Research, 330 (3): 365-372 (2001); Picout and Ross-Murphy 2002). The polydispersity ($M_w/M_n$) did not change during enzymatic hydrolysis until 10 μL enzyme/g BFG was used and the polydispersity increased presumably due to the release of smaller arabinoxylan fragments.

TABLE 3

Molecular characteristics of original and hydrolyzed BFG products as measured using HPSEC-MALS-RI and viscometric detection

| Sample | $M_w \times 10^3$ (Da) | $M_w/M_n$ | $Iv_w$ (mL/g) | $R_{gz}$ (nm) | a |
|---|---|---|---|---|---|
| BFG original | 253 ± 3 | 1.37 ± 0.04 | 1.11 ± 0.01 | 30.9 ± 3 | 0.605 ± 0.02 |
| BFGH-1 | 132 ± 3 | 1.34 ± 0.05 | 0.726 ± 0.01 | 23 ± 1 | 0.843 ± 0.02 |
| BFGH-5 | 92.7 ± 1 | 1.35 ± 0.05 | 0.518 ± 0.001 | 22.8 ± 2 | 0.855 ± 0.01 |
| BFGH-10 | 51.6 ± 0.1 | 1.96 ± 0.1 | 0.295 ± 0.004 | 19.8 ± 1 | 0.777 ± 0.02 |

Figure 3:
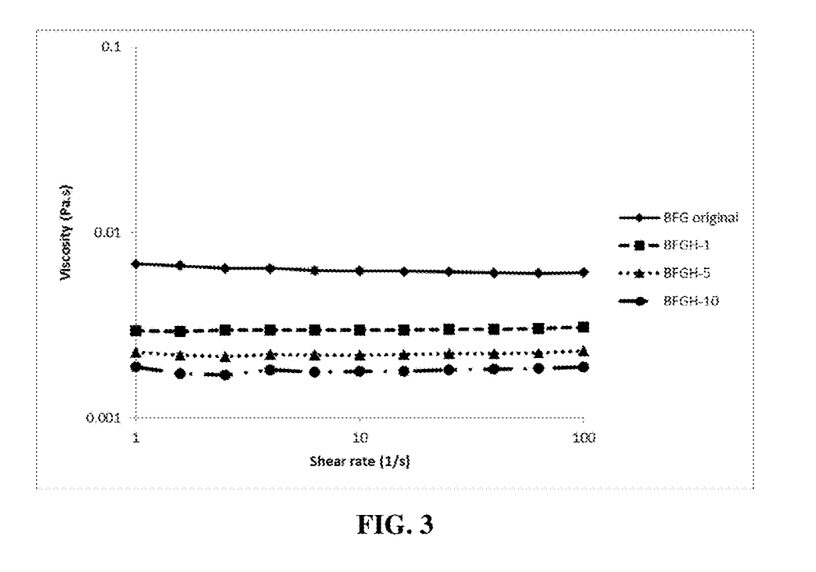
FIG. 3 shows flow curves of 2% solutions of BFG and BFG hydrolyzates as described below.

Flow behavior: FIG. 3 shows the flow curves of 2% solutions of the BFG and its hydrolyzates. It is clear that all the solutions exhibited Newtonian flow behavior with the viscosity remaining constant and independent of shear rate. This is in contrast to the report by Rumpagaporn et al. (2012), which showed that the endoxylanase hydrolyzate of corn bran arabinoxylan showed marked shear thinning flow behavior. Without being bound by theory, this difference could be a result of the higher concentration of hydrolyzate (5% and 10% as against 2% in the current study) or could be related to the use of a different endoxylanase enzyme which gave a different molecular shape of the product. In fact, the BFG hydrolyzates in the current study did show slight shear thinning behavior at 5% concentration (data not shown), although the extent of shear thinning was still less than that observed by Rumpagaporn et al. (2012).

As the enzyme concentration increased surprisingly the viscosity of BFG hydrolyzates progressively decreased (FIG. 3). This result represents another advantage to the use of BFG hydrolyzates as dietary fiber sources for use in food systems, since low viscosity is a highly desirable characteristic in this context. While most of the low viscosity dietary fibers tend to be simple, low molecular weight materials (e.g., fructooligosaccahrides or galactooligosaccharides), the BFG hydrolyzates have the significant added advantage of complex structure and polymeric nature which combined to impart desirable colonic fermentation properties to this material (Hamaker et al., 2014, U.S. patent application Ser. No. 12/791,802).

Figure 4:
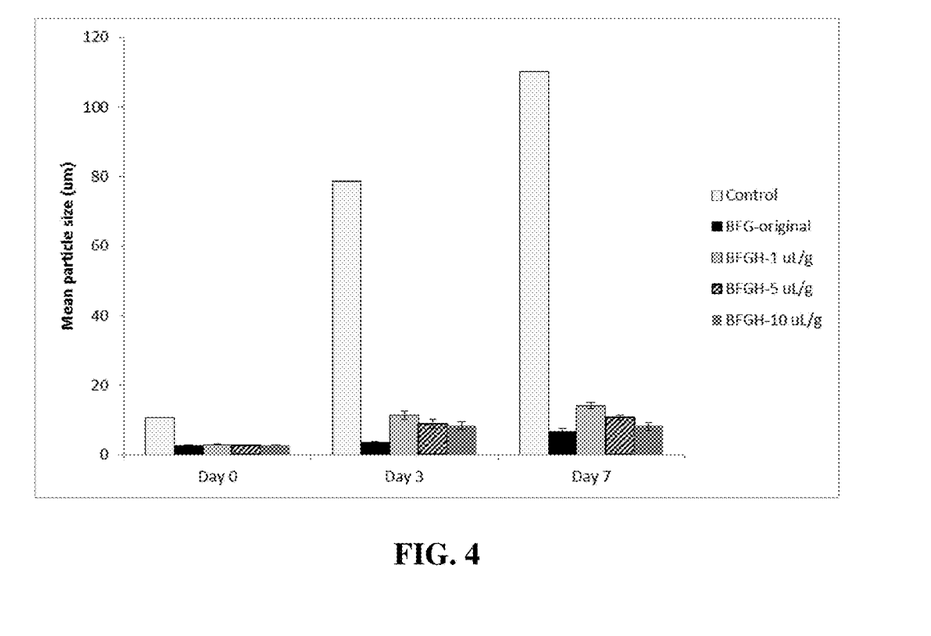
FIG. 4 shows mean particle size of oil droplets in emulsions of Medium Chain Triglyceride (MCT) oil in water stabilized by BFG and BFG hydrolyzates over 7 days of incubation at 60° C. as described below.

Emulsifying property: FIG. 4 shows the mean particle size of oil droplets in an oil-in-water emulsion stabilized using BFG and the different BFG hydrolyzates in comparison to a no emulsifier control. The values of mean particle size are also given in Table 4. All of the samples except the control showed similar particle size on Day 0, indicating similar emulsifying ability. It was surprising that the hydrolysis process did not affect this property of the BFG hydrolyzates. Without being bound by theory, this may be related to the polymeric nature of the hydrolyzates which still retained the molecular complexity that plays a role in the emulsifying property. In this context, the inability of the endoxylanase to further hydrolyze corn BFG into oligosaccharides may actually have proven to be an advantage as the endoxylanase hydrolyzed the material enough to improve functional properties (e.g., solubility and viscosity) but not so much as to lose its unique emulsifying ability. It is also very interesting to note that all the emulsions showed similar particle sizes over the entire week of incubation at 60° C., indicating that the hydrolysis process surprisingly did not affect the emulsion stability to a large extent.

TABLE 4

Mean particle size values for oil droplets in emulsions of MCT oil in water stabilized by BFG and BFG hydrolyzates over 7 days of incubation at 60° C.

| | Mean particle size (μm) | | |
|---|---|---|---|
| Sample | Day 0 | Day 3 | Day 7 |
| Control | 10.48 | 78.66 | 110.11 |
| BFG-original | 2.48 ± 0.18 | 3.55 ± 0.15 | 6.46 ± 1.11 |
| BFGH-1 | 2.86 ± 0.20 | 11.26 ± 1.23 | 14.12 ± 0.93 |
| BFGH-5 | 2.72 ± 0.81 | 8.74 ± 1.29 | 10.59 ± 0.71 |
| BFGH-10 | 2.73 ± 0.06 | 8.26 ± 1.12 | 8.23 ± 1.51 |

Conclusions: It was found that endoxylanase hydrolysis, using a commercially available enzyme preparation, was a surprisingly effective way to improve solubility and solution characteristics without affecting the emulsifying ability of Bio-Fiber Gum (e.g., from corn). The surprisingly good emulsifying properties of the hydrolyzates will allow their use as multifunctional ingredients in food systems wherein they can be incorporated in large amounts for fiber fortification, owing to their high solubility and low viscosity, and can also replace emulsifiers and offer a clean label. It is noteworthy that Bio-Fiber Gum itself offers all of these functionalities in its own right, but the BFG hydrolyzates surprisingly further improved the solubility and solution characteristics without negatively affecting other physical or physiological functionalities. The clarity of BFGH solutions will also enable their use in food systems where this is a concern, such as clear beverages. Thus, BFG and BFG hydrolyzates together represent a range of dietary fiber ingredients with different molecular weights and solution characteristics, all of which offer excellent functional properties and health benefits. Besides outlining processes to produce arabinoxylan hydrolyzates from commercially available raw materials in a scalable process, this study represents a potential technology to produce hydrolyzates from different Bio-Fiber Gums, such as those from wheat and other cereal brans, to produce polymeric or oligomeric hydrolyzates which will be excellent ingredients for fiber fortification of foods.

Thus in spite of hydrolysis to a lower molecular weight, our material surprisingly has similar emulsification properties as the original BFG. It also surprisingly has improved solubility and low viscosity relative to the original BFG.

All of the references cited herein, including U.S. patents and U.S. patent application Publications, are incorporated by reference in their entirety. Also incorporated by reference in their entirety are the following references: U.S. patent application Ser. No. 13/798,468 filed on 13 Mar. 2013 (including amendments to the claims thereof); Broekaert, W. F., et al., Critical Reviews in Food Science and Nutrition, 51 (2): 178-194 (2011); Cloetens, L., et al., British Journal of Nutrition, 103 (5): 703-713 (2010); Delcour, J. A., et al., Trends in Food Science and Technology, 25 (2): 78-86 (2012); Francois, I. E. J. A., et al., Journal of Pediatric Gastroenterology and Nutrition, 58 (5): 647-653 (2014); Grootaert, C., et al., Microbiology Ecology: 61, 231-242 (2009); Hamaker et al., 2014, U.S. patent application Ser. No. 12/791,802; Rumpagaporn, P., et al., Journal of Food Science, 71 (1): H23-H30 (2012); Saha, B. C., and R. J. Bothast, Enzymology of Xylan Degradation Biopolymers, American Chemical Society, Washington, D.C., pp. 167-194 (1999); Swennen, K., et al., Journal of the Science of Food and Agriculture, 86 (11): 1722-1731 (2006); Verbruggen, M. A., et al., Carbohydrate Research, 306 (1-2): 265-274 (1998).

Thus, in view of the above, there is described (in part) the following:

A process to hydrolyze bio-fiber gum (BFG), said method comprising (or consisting essentially of or consisting of) dissolving BFG in a solvent at pH of about 2.5 to about 7 to form a solution, heating said solution (e.g., to about 20° to about 70° C.) and adding endoxylanase to said solution or adding endoxylanase to said solution and heating said solution (e.g., from about 20° C. to about 70° C.), incubating said solution from about 20° C. to about 70° C. for about 30 minutes to about 24 hours to form a solution containing BFG hydrolysate, boiling said solution containing BFG hydrolysate for about 5 minutes to about 30 minutes to inactivate said endoxylanase, and separating said BFG hydrolysate from the liquid in said solution containing BFG hydrolysate.

A process to hydrolyze bio-fiber gum (BFG), said method comprising (or consisting essentially of or consisting of) dissolving BFG in a solvent at pH of about 2.5 to about 7 to form a solution, heating said solution (e.g., from about 20° C. to about 70° C.) and adding endoxylanase to said solution or adding endoxylanase to said solution and heating said solution (e.g., from about 20° C. to about 70° C.), incubating said solution (e.g., from about 20° C. to about 70° C.) for about 15 minutes to about 36 hours (e.g., 15 minutes to 36 hours; preferably about 30 minutes to about 24 hours (e.g., 30 minutes to 24 hours) to form a solution containing BFG hydrolysate, boiling said solution containing BFG hydrolysate for about 1 minute to about 60 minutes (e.g., 1 minute to 60 minutes; preferably about 5 minutes to about 30 minutes (e.g., 5 minutes to 30 minutes)) to inactivate said endoxylanase, and separating said BFG hydrolysate from the liquid in said solution containing BFG hydrolysate. The above process, wherein about 5 IU to about 6000 IU of said endoxylanase is added per gram of said BFG. The above process, wherein about 10 IU to about 3000 IU of said endoxylanase is added per gram of said BFG. The above process, wherein about 20 IU to about 600 IU of said endoxylanase is added per gram of said BFG. The above process, wherein about 60 IU to about 120 IU of said endoxylanase is added per gram of said BFG.

The above process, wherein said BFG is produced by a method comprising (or consisting essentially of or consisting of): (a) mixing agricultural materials (e.g., corn bran/fiber or other bran/fiber samples such as oat bran, wheat bran, barley straw and hull, sugar cane bagasse, corn stover, wheat straw, sorghum bran) and/or lignocellulosic energy crops (e.g., switchgrass and miscanthus); the term "agricultural materials" is defined herein as including agricultural products, lignocellulosic agricultural by-products, and lignocellulosic energy crops, individually or as mixtures) with a heated alkaline solution at temperatures in the range of about 75° to about 150° C. to form a slurry; (b) separating out the insoluble components from said slurry to yield a solution having a pH of about 9 to about 14 wherein said solution contains about 0.1 to about 10 wt % solids wherein said solids are alkaline soluble fractions; and one of the following: (c) evaporating said solution to about 16 to about 23 wt % solids and drying to a powder; (d) adjusting the pH of said solution to a pH of about 2 to about 12, evaporating said solution to about 16 to about 23 wt % solids and drying to a powder; (e) evaporating said solution to about 16 to about 23 wt % solids, adjusting the pH of said solution to a pH of about 2 to about 12 and drying to a powder; (f) evaporating said solution to about 16 to about 23 wt % solids and precipitating out said soluble components with about two to about five volumes of solvent to form a precipitate and a supernatant, and separately drying said precipitate and said supernatant; (g) evaporating said solution to about 16 to about 23 wt % solids, adjusting the pH of said solution to a pH of about 2 to about 12 and precipitating out said soluble components with one to five volumes of organic solvent to form a precipitate and a supernatant, and separately drying said precipitate and said supernatant; (h) adjusting the pH of said solution to a pH of about 2 to about 12, evaporating said solution to about 16 to about 23 wt % solids and precipitating out said soluble components with about one to five volumes of organic solvent to form a precipitate and a supernatant, and separately drying said precipitate and said supernatant; or (i) adjusting the pH of said solution to a pH of about 2 to about 5 to precipitate Hemicellulose A and the remaining solution is treated with about 2 volumes of solvent to form a precipitate and a supernatant, and separately drying said precipitate and said supernatant; and optionally the solution is pretreated with at least one of the following: (1) de-salting said solution and the de-salted solution becomes the solution; (2) processing said solution through at least one nano-filtration membrane or ultra-filtration membrane or diafiltration membrane and the permeate becomes the solution; or (3) processing said solution through at least one nano-filtration membrane or ultra-filtration membrane or diafiltration membrane and the retentate becomes the solution; wherein said process does not utilize oxidizing agents and wherein said product contains feruloyl-arabinoxylans.

Bio-fiber gum hydrolyzate, said bio-fiber gum hydrolyzate produced by the above process. The above bio-fiber gum hydrolysate, wherein said bio-fiber gum hydrolysate has molecular weight of about 200 Da to about 40 kDa.

An oil-in-water or water-in-oil composition comprising (or consisting essentially of or consisting of) (a) a product produced by the above process as an emulsifier, (b) oil and (c) water.

A composition comprising (or consisting essentially of or consisting of) (a) a product produced by the above process as a binder and (b) carbonaceous materials.

A composition comprising (or consisting essentially of or consisting of) (a) a product produced by the above process as an antioxidant and (b) a material that is oxidizable.

A method of reducing oxidation of a composition that is oxidizable, said method comprising (or consisting essentially of or consisting of) adding the product produced by the above process to a composition that is oxidizable.

A method of binding carbonaceous materials, said method comprising (or consisting essentially of or consisting of) adding the product produced by the above process to carbonaceous materials, and pelletizing.

A method for stabilizing an oil-in-water or water-in-oil emulsion, said method comprising (or consisting essentially of or consisting of) adding the product produced by the above process to oil and water.

A method for producing plywood with less phenol-formaldehyde resin, said method comprising (or consisting essentially of or consisting of) adding the product produced by the above process to plywood formulations, pressing and heating.

A method of stabilizing oxidizable material (e.g., oils, flavors, and fragrances), said method comprising (or consisting essentially of or consisting of) adding the product produced by the above process to the oxidizable material to form an emulsion and spray drying to form an encapsulated product.

The term "consisting essentially of" excludes additional method (or process) steps or composition components that substantially interfere with the intended activity of the method (or process) or composition.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

The claimed invention is:

1. A process to hydrolyze bio-fiber gum (BFG), said process comprising: (a) dissolving BFG in a solvent at pH of about 2.5 to about 7 to form a solution; (b) heating said solution and adding endoxylanase to said solution or adding endoxylanase to said solution and heating said solution; (c) incubating said solution to a temperature in a range from about 20° C. to about 70° C. to form a solution containing BFG hydrolysate; (d) boiling said solution containing BFG hydrolysate to inactivate said endoxylanase; and (e) separating said BFG hydrolysate from the liquid in said solution containing BFG hydrolysate.

2. The process according to claim 1, wherein about 5 IU to about 6000 IU of said endoxylanase is added per gram of said BFG.

3. The process according to claim 1, wherein about 10 IU to about 3000 IU of said endoxylanase is added per gram of said BFG.

4. The process according to claim 1, wherein about 20 IU to about 600 IU of said endoxylanase is added per gram of said BFG.

5. The process according to claim 1, wherein about 60 IU to about 120 IU of said endoxylanase is added per gram of said BFG.

6. The process according to claim 1, wherein said BFG is produced by a method comprising: (a) mixing agricultural materials with a heated alkaline solution at temperatures in the range of about 75° C. to about 150° C. to form a slurry and (b) separating out the insoluble components from said slurry to yield a solution having a pH of about 9 to about 14 wherein said solution contains about 0.1 to about 10 wt % solids wherein said solids are alkaline soluble fractions.

7. The process of claim 6 further comprising evaporating said solution of step (b) to about 16 to about 23 wt % solids and drying to a powder.

8. The process of claim 6 further comprising adjusting the pH of said solution of step (b) to a pH of about 2 to about 12, evaporating said solution to about 16 to about 23 wt % solids, and drying to a powder.

9. The process of claim 6 further comprising evaporating said solution of step (b) to about 16 to about 23 wt % solids, adjusting the pH of said solution to a pH of about 2 to about 12, and drying to a powder.

10. The process of claim 6 further comprising evaporating said solution of step (b) to about 16 to about 23 wt % solids and precipitating out said soluble components with about two to about five volumes of solvent to form a precipitate and a supernatant, and separately drying said precipitate and said supernatant.

11. The process of claim 6 further comprising evaporating said solution of step (b) to about 16 to about 23 wt % solids, adjusting the pH of said solution to a pH of about 2 to about 12, and precipitating out said soluble components with one to five volumes of organic solvent to form a precipitate and a supernatant, and separately drying said precipitate and said supernatant.

12. The process of claim 6 further comprising adjusting the pH of said solution of step (b) to a pH of about 2 to about 12, evaporating said solution to about 16 to about 23 wt % solids and precipitating out said soluble components with about one to five volumes of organic solvent to form a precipitate and a supernatant, and separately drying said precipitate and said supernatant.

13. The process of claim 6 further comprising adjusting the pH of said solution of step (b) to a pH of about 2 to about 5 to precipitate Hemicellulose A and the remaining solution is treated with about 2 volumes of solvent to form a precipitate and a supernatant, and separately drying said precipitate and said supernatant.

14. The process of claim 6 further comprising pretreating the solution of step (b) with at least one of the following: (1) de-salting said solution and the de-salted solution becomes the solution; (2) processing said solution through at least one nano-filtration membrane or ultra-filtration membrane or diafiltration membrane and the permeate becomes the solution; or (3) processing said solution through at least one nano-filtration membrane or ultra-filtration membrane or diafiltration membrane and the retentate becomes the solution; wherein said process does not utilize oxidizing agents and wherein said product contains feruloyl-arabinoxylans.

15. A composition comprising a bio-fiber gum hydrolyzate, said bio-fiber gum hydrolyzate produced by the process of claim 1.

16. The composition according to claim 15, wherein said bio-fiber gum hydrolysate has a molecular weight of about 200 Da to about 40 kDa.

17. The composition of claim 15, further comprising forming an oil-in-water or water-in-oil composition comprising (a) said bio-fiber gum hydrolyzate as an emulsifier, (b) oil, and (c) water.

18. The composition of claim 15, wherein said bio-fiber gum hydrolysate is (i) a binder for carbonaceous materials or (ii) an antioxidant.

19. The composition of claim 18, further comprising reducing oxidation of an oxidizable composition by adding said bio-fiber gum hydrolysate the oxidizable composition.

20. A method of binding carbonaceous materials, said method comprising (a) adding a product produced by the process of claim 1 to a carbonaceous material and pelletizing or (b) producing plywood with less phenol-formaldehyde resin by adding a product produced by the process of claim 1 to a plywood formulation, pressing the plywood formulation, and heating to create plywood from the plywood formulation.

21. The process of claim 1, further comprising incubating said solution to a temperature in a range from about 20° C. to about 70° C. for about 15 minutes to about 36 hours.

22. A composition comprising a bio-fiber gum hydrolysate having a similar emulsifying ability as a bio-fiber gum which has not been hydrolyzed.

23. The composition of claim 22, wherein the bio-fiber gum hydrolysate has at least one property selected from the group consisting of: a polydispersity index of about 1.3 to about 2; a weight average intrinsic viscosity of about 0.3 mL/g to about 1 mL/g; an average radius of gyration of about 20 nm to about 25 nm; a Mark Houwink Constant of about 0.7 to about 0.9.

24. The composition of claim 22, further comprising an average molar mass from about 50 kDa to about 135 kDa.

25. The composition of claim 22, further comprising a molecular weight from about 200 Da to about 40 kDa.

26. The composition of claim 22, further comprising a mean particle size for oil droplets if in an emulsion with one or more medium chain triglycerides from about 2.5 μm to about 15 μm.

27. The process of claim 1, further comprising boiling said solution containing BFG hydrolysate for about 1 minute to about 60 minutes to inactivate said endoxylanase.

\* \* \* \* \*